(12) United States Patent
Rothman et al.

(10) Patent No.: US 6,605,464 B1
(45) Date of Patent: Aug. 12, 2003

(54) METHOD OF TREATMENT OF CANCER AND INFECTIOUS DISEASE AND COMPOSITIONS USEFUL IN SAME

(75) Inventors: James E. Rothman, New York, NY (US); F. Ulrich Hartl, Munich (DE); Mee H. Hoe, New York, NY (US); Alan Houghton, New York, NY (US); Yoshizumi Takeuchi, New York, NY (US); Mark Mayhew, Tarrytown, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 0 days.

(21) Appl. No.: 09/511,453

(22) Filed: Feb. 23, 2000

Related U.S. Application Data

(62) Division of application No. 09/011,648, filed as application No. PCT/US96/13233 on Aug. 16, 1996, now Pat. No. 3,331,299.
(60) Provisional application No. 60/002,479, filed on Aug. 18, 1995, and provisional application No. 60/002,490, filed on Aug. 18, 1995.

(51) Int. Cl.[7] ............................................. C12N 15/63
(52) U.S. Cl. .................. 435/320.1; 435/69.1; 435/455; 435/325
(58) Field of Search ............................. 435/320.1, 325, 435/455, 458, 69.1

(56) References Cited

U.S. PATENT DOCUMENTS

| | | | |
|---|---|---|---|
| 5,348,945 A | 9/1994 | Berberian et al. | |
| 5,750,119 A | 5/1998 | Srivastava et al. | |
| 5,961,979 A | 10/1999 | Srivastava | 424/193.1 |
| 6,075,358 A1 | 9/2001 | Podack et al. | |

FOREIGN PATENT DOCUMENTS

| | | | |
|---|---|---|---|
| EP | 0 538 952 | | 4/1993 |
| WO | 9317712 | | 9/1993 |
| WO | WO 94/11513 | * | 5/1994 |
| WO | 9411513 | | 5/1994 |
| WO | 94-29459 | * | 12/1994 |
| WO | 9429459 | | 12/1994 |
| WO | 9524923 | | 9/1995 |
| WO | 9610411 | | 4/1996 |
| WO | 9706685 | | 2/1997 |
| WO | 9706821 | | 2/1997 |
| WO | 9710000 | | 3/1997 |
| WO | 9710001 | | 3/1997 |
| WO | 9710002 | | 3/1997 |
| WO | 9726910 | | 7/1997 |
| WO | 9942121 | | 8/1999 |

OTHER PUBLICATIONS

Ngo et al., Computational Complexity Protein Structure Prediction and the Levinthal Paradox, 1994, Birkhauser Boston, vol. 14, pp. 491–495.*

Huang, et al., 2000, In Vivo Cytotoxic T Lymphocytes Elicitation by Mycobacterial Heat Shock Protein 70 Fusion Proteins Maps to a Discrete Domain and Is CD4[30] T Cell Independent, J.. Exp. Med., 191:403–408.

Todryk et al., 1999, Heat Shock Protein 70 Induced During Tumor Cell Killing Induces Th1 Cytokines and Targets Immature Dendritic Cell Precursors to Enhance Antigen Uptake, J. Immunology, 163:1398–1408.

Yamazaki et al., 1999, Cutting Edge:Tumor Secreted Heat Shock–Fusion Protein Elicits CD8 Cells for Rejection, J. Immunology 163:5178–5182.

Melcher et al., 1998, Tumor Immonogenicity is Determined by the Mechanism of Cell Death Via Induction of Heat Shock Protein Expression, Nature Medicine 4:581–587.

Wells, et al., 1998, Hsp72–mediated Augmentation of MHC Class I Surface Expression and Endogenous Antigen Presentation, Int. Immunol 10:609–617.7.

Auger, et al., 1996, HLA–DR4 and HLA–DR10 Motifs That Carry Susceptibility to Rheumatoid Arthritis Bind 70–KD heat Shock Proteins, Nature Medicine 2:306–310.

Giboa, 1996, Immunotherapy of Cancer With Genetically Modified Tumor Vaccines, Seminars in Oncology 23:101–107.

Mastrangelo, et al., 1996, Gene Therapy for Human Cancer: An Essay for Clinicians, Seminars in Oncology, 23:4–21.

Minami et al., 1996, Regualatin of the Heat–shock Protein 70 Reaction Cycle by the Mammalian DnaJ Homolog, Hsp40, J. Biol. Chem. 271:19617–19624.

Nieland, et al., 1996, Isolation of an Immunodominant Viral Peptide that is Endogenously Bound to the Stress Protein GP96/GRP94, Proc. Natl. Acad. Sci. USA 93:6135–6139.

Zhu, et al., 1996, Structural Analysis of Substrate Binding by the Molecular Chaperone DnaK, Science 272:1606–1614.

Bauer, et al., 1995, Scand. J. Immunol. 42:317–323.Identification of H–2K[β] Binding and Immunogenic Peptides from Human Papilloma Virus Tumour Antigens E6 and E7.

Blachere and Srivastava, 1995, Heat Shock Protein–based Cancer Vaccines and Related thoughts on Immunogenicity of Human Tumors, Seminars in Cancer Biology 6:349–355.

(List continued on next page.)

Primary Examiner—Dave T. Nguyen
(74) Attorney, Agent, or Firm—Kenyon & Kenyon

(57) ABSTRACT

Administration of expressible polynucleotides encoding eukaryotic heat shock proteins to mammalian cells leads to the stimulation of an immune response to antigens present in those cells. This makes it possible to stimulate an immune response to target antigens, including target tumor antigens or antigens associated with an infectious disease, without having to isolate a unique antigen or antigen-associated heat shock protein for each target antigen by administering to a mammalian subject or to a group of mammalian cells containing the antigen, an expressible polynucleotide encoding a heat shock protein. The expressed heat shock protein may have the same structure as native heat shock proteins, or may have a modified form adapted to control the trafficking of the expressed heat shock protein within the cells.

3 Claims, 5 Drawing Sheets

OTHER PUBLICATIONS

Edginton, 1995, Therapeutic Applications of Heat Shock Proteins, Bio/Technol. 13:1442–1444.

Greene et al., 1995, Effect of Nucleotide on the Binding of Peptides to 70–kDa Heat Shock Protein, J. Biol. Chem. 270:2967–2978.

Hohfeld et al., 1995, Hip, a Novel Cochaperone Involved in the Eukaryotic Hsc70/Hsp40 Reaction Cycle, Cell 83:589–598.

Lowrie et al., 1995, Keystone Symposium on Heat Shock (Stress) Protein in Biology and Medicine, J. Cell. Biochem. Suppl. 0(19b):220.

McCarty et al., 1995, The Role of ATP in the Functional Cycle of the DnaK Chaperone System, J. Mol. Biol. 249:126–137.

Multhoff, et al., 1995, Int. J. Cancer 61:272–279.A Stress––Inducible 72–kDa Heat–Shock Protein (HSP72) is Expressed on the Surface of Human Tumor Cells, But Not On Normal Cells.

Zhu, et al., 1995, Both Immunization with Protein and Recombinant Vaccinia Virus Can Stimulate CTL Specific for the E7 Protein of Human Papilloma Virus 16 in H–$2^d$ Mice, Scand. J. Immunol. 42:557–563.

Barrios et al., 1994, Specificity of Antibodies After Immunization of Mice with the Mycobacterial Heat Shock Protein oj 65 kD, Clin. Exp. Immunol. 98:224–228.

Barrios et al., 1994, Clin. Exp. Immunol. 98:229–233.Heat Shock Proteins as Carrier Molecules: in vivo Helper Effect Mediated by *Escherichia coli* GroEL and DnaK Proteins Requires Cross–Linking with Antigen.

Del Guidice, 1994, Hsp/70: a carrier molecule with built–in adjuvanticity, Experientia 50:1061–1066.

Lowrie et al., 1994, Towards a DNA vaccine against tuberculosis, Vaccine 12:1537–1540.

Nygren, et al., 1994, Engineering proteins to facilitate bioprocessing, Trends Biotechnol. 12(5):184–188.

Retzlaff et al., 1994, Infect. Immun. 62:5689–5693.Bacterial Heat Shock Proteins Directly Induce Cytokine mRNA and Interleukin–1 Secretion in Macrophage Cultures.

Schmid et al., 1994, Kinetics of Molecular Chaperone Action, Science 263:971–973.

Barrios, et al., 1992, Mycobacterial heat–shock proteins as carrier molecules. II: The use of the 70–kDa mycobacterial heat–shock protein as carrier for conjugated vaccines can circumvent the need for adjuvants and Bacillus Calmette Guérin priming, Euro. J. Immunol. 22:1365–1372.

Davidoff, et al., 1992, Immune response to p53 is dependent upon p53/HSP70 complexes in breast cancers, Proc. Nat'l. Acad. Sci. USA, 89:3439–3442.

Pidoux et al., 1992, Analysis of the BiP gene and identification of an ER retention signal in *Schizosaccharomyces pombe*, EMBO J. 11:1583–1591.

Lussow, et al., 1991, Mycobacterial heat–shock proteins as carrier molecules, J. Eur. Immunolo. 21:2297–2302.

Srivastava and Maki, 1991, Stress–Induces Proteins in Immune Response to Cancer, Current Topics in Microbiology and Immunology, 167:109–121.

Flajnik et al., 1991, Which Came First, MHC Class 1 or Class II?, Immunogenetics, 33:295–300.

Flynn et al., 1989, Peptide Binding and Release by Proteins Implicated as Catalysis of Protein Assembly, Science 245:385–390.

Pelham, 1988, Evidence that luminal ER proteins are sorted from secreted proteins in a post–ER compartment, EMBO J. 7:913–918.

Munro and Pelham, 1987, A C–Terminal Signal Prevents Secretion of Luminal ER Proteins, Cell, 480:899–907.

Srivastava, et al., 1986, Tumor rejection antigens of chemically induced sarcomas of inbred mice, Proc. Natl. Acad. Sci. USA, 83:3407–3411.

Ullrich, et al., Proc. 1986, A mouse tumor–specific transplantation antigen is a heat shock–related protein, Proc. Natl. Acad. Sci. U.S.A., 83:3121–3125.

Von Heijne, 1985, Signal Sequences The Limits of Variation, J. Mol. Biol. 184:99–105.

Melcher et al., 1998, Tumor Immunogenicity is Determined by the Mechanisms of Cell Death Via Induction of Heat Shock Protein Expression, Nature Medicine 4:581–587.

Wells, et al., 1998, Hsp72–mediated Augmentation of MHC Class I Surface Expression and Endogenous Antigen Presentation, Int. Immunol 10:609–617.7.

Dillmann et al., 1995, Heat Shock Proteins and Ischemic Injury, J. Cell. Biochem., Suppl. 19B, p . 190, Abstract B6–015.

Plumier et al., 1995, *Transgenic Mice Expressing the Human Heat Shock Protein 70 Have Improved Post–Ischemic Myocardial Recovery*, J. Clin. Invest. 95:1854–1860.

Little et al., 1994, *The Glucose–Regulated Proteins (GRP78 and GRP94): Functions, Gene Regulation, and Applications*, Crit. Rev. Eukaryot. Gene Expr. 4:1–18.

Li et al., 1993, *Tumor Rejection Antigen gp96/grp94 is an ATPase: Implications for Protein Folding and Antigen Presentation*, EMBO J. 12(8):3143–3151.

Porgador et al., 1994, *Immunotherapy of Tumor Metastasis via Gene Therapy*, Nat. Immun. 13:113–130.

Jäättelä, 1995, *Over–Expression of hsp70 Confers Tumorigenicity to Mouse Fibrosarcoma Cells*, Int. J. Cancer 60:689–693.

Udono et al., 1994, *Comparison of Tumor–Specific Immunogenicities of Stress–Induced Proteins gp96, hsp90, and hsp70*, J. Immunol. 152:5398–5403.

Udono et al., 1993, *Heat Shock Protein70–Associated Peptides Elicit Specific Cancer Immunity*, J. Exp. Med. 178:1391–1396.

Pardoll, 1993, *New Strategies for Enhancing the Immunogenicity of Tumors*, Curr. Opin. Immunol. 5:719–725.

Sato et al., 1994, *Immunology/Biological Therapy*, Proc. Annu. Meet. Am. Assoc. Cancer Res. 35:A2959.††

Silva and Lowrie, 1994, *A single mycobacterial protein (hsp65) expressed by a transgenic antigen–presenting cell vaccinates mice against tuberculosis*, Immunology 82:244–248.

Srivastava, 1994, *Heat shock proteins in immune response to cancer: The Fourth Paradigm*, Experentia 50:1054–1060.

Srivastava and Udono, 1994, *Heat shock protein–peptide complexes in cancer immunotherapy*, Current Opinion in Immunology 6:728–732.

Lukas, et al., 1994, *Protection Against Tumour by Transfer of Mycobacterial Heat Shock Protein Gene*, Cancer Gene Therapy, 1:217.

Blond–Elguindi et al., 1993, *Affinity Panning of a Library of Peptides Displayed on Bacteriophages Reveals the Binding Specificity of BiP*, Cell 75:717–728.

DeNagel and Pierce, et al., 1993, *Heat Shock Proteins in Immune Responses*, Critical Reviews in Immunology 13:71–81.

Lukacs et al., 1993, *Tumor Cells Transfected with a Bacterial Heat–Shock Gene Lose Tumorigenicity and Induce Protection against Tumors*, J. Exp. Med. 178:343–348.

Mustafa, et al., 1993, *Human T. Cells Recognize Mycobacterial Heat Shock Proteins in the Context of Multiple HLA–DR Molecules: Studies with Healthy Subject Vaccinated with Mycobacterium bovis BCG and Mycobacterium leprae*, Infection and Immunity 61:5294–5301.

Palleros et al., 1993, *ATP–induced protein–Hsp70 complex dissoclation requires K but not ATP hydrolsis*, Nature 365:664–666.

Perraut, 1993, Clin Exp. Immunol. 93:382–386.Successful primate immunization with peptides conjugated to purified protein derivative or mycobacterial heat shock proteins in the absence of adjuvants.

Srivastava, 1993, *Peptide–Binding Heat Shock Proteins in the Endoplasmic Reticulum: Role in Immune Response to Cancer and in Antigen Presentation*, Adv. Cancer Res. 62:153–177.

Yamamoto, et al., 1993, *Listeria monocytogenes–Induced Gamma Interferon Secretion by Intestinal Intraepithelial T Lymphocytes*. Infection and Immunity 61:2154–2161.

* cited by examiner

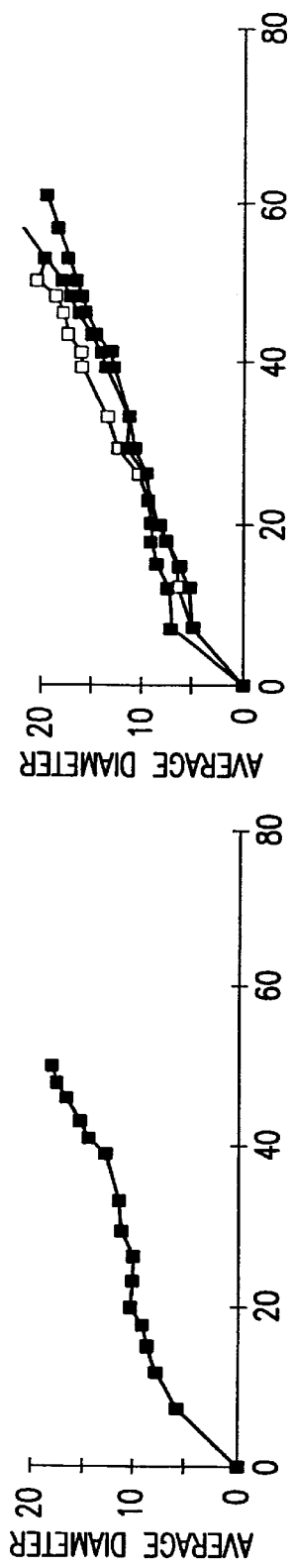
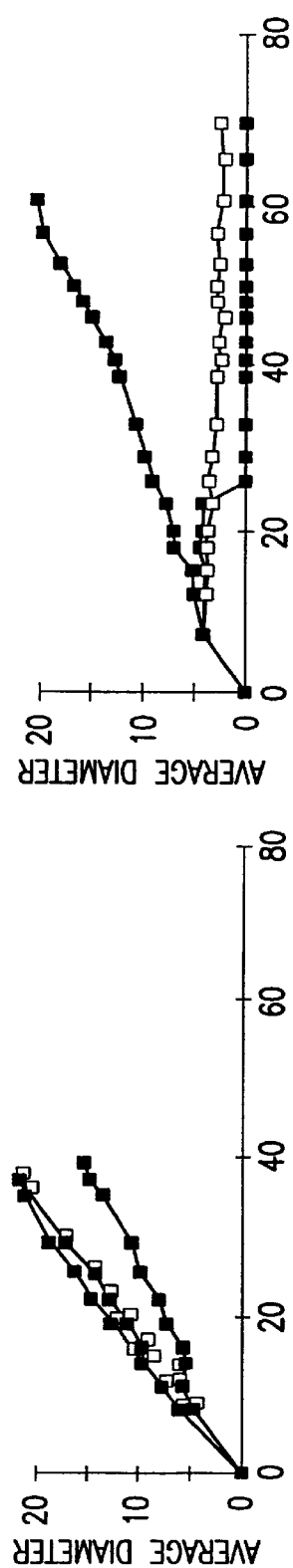

METHOD OF TREATMENT OF CANCER AND INFECTIOUS DISEASE AND COMPOSITIONS USEFUL IN SAME

The present application is a divisional application of U.S. patent application Ser. No. 09/011,648, now U.S. Pat. No. 6,331,299, which is based on International Application No. PCT/US96/13233, filed Aug. 16, 1996, which is based on provisional U.S. Application Nos. 60/002,479 and 60/002,490, both filed on Aug. 18, 1995.

The invention described herein was made in the course of work under NIH Core Grant No. CA 08748. The United States government may have certain rights in this invention.

BACKGROUND OF THE INVENTION

This application relates to the use of heat shock proteins and similar peptide-binding proteins to stimulate an immunological response against antigens, including cancer-related antigens, autoimmune antigens and infectious disease antigens, found in a mammalian host.

Heat shock proteins were originally observed to be expressed in increased amounts in mammalian cells which were exposed to sudden elevations of temperature, while the expression of most cellular proteins is significantly reduced. It has since been determined that such proteins are produced in response to various types of stress. including glucose deprivation. As used herein, the term "heat shock protein" will be used to encompass both proteins that are expressly labeled as such as well as other stress proteins, including homologs of such proteins that are expressed constitutively (i.e., in the absence of stressful conditions). Examples of heat shock proteins include BiP (also referred to as grp78), hsp/hsc70, gp96 (grp94), hsp60, hsp40 and hsp90.

Heat shock proteins have the ability to bind other proteins in their non-native states, and in particular to bind nascent proteins emerging from the ribosomes or extruded into endoplasmic reticulum. Hendrick and Hartl, *Ann. Rev. Biochem.* 62: 349–384 (1993); Hartl, *Nature* 381: 571–580 (1996). Further, heat shock proteins have been shown to play an important role in the proper folding and assembly of proteins in the cytosol, endoplasmic reticulum and mitochondria; in view of this function, they are referred to as "molecular chaperones". Frydman et al., *Nature* 370: 111–117 (1994); Hendrick and Hartl., *Ann. Rev. Biochem.* 62:349–384 (1993); Hartl., *Nature* 381:571–580 (1996).

For example, the protein BiP, a member of a class of heat shock proteins referred to as the hsp70 family, has been found to bind to newly synthesized, unfolded u immunoglobulin heavy chain prior to its assembly with light chain in the endoplasmic reticulum. Hendershot et al.,*J. Cell Biol.* 104:761–767 (1987). Another heat shock protein, gp96, is a member of the hsp90 family of stress proteins which localize in the endoplasmic reticulum. Li and Srivastava, *EMBO J.* 12:3143–3151 (1993); Mazzarella and Green,*J. Biol. Chem.* 262:8875–8883 (1987). It has been proposed that gp96 may assist in the assembly of multi-subunit proteins in the endoplasmic reticulum. Wiech et al., *Nature* 358:169–170 (1992).

It has been observed that heat shock proteins prepared from tumors in experimental animals were able to induce immune responses in a tumor-specific manner; that is to say, heat shock protein purified from a particular tumor could induce an immune response in an experimental animal which would inhibit the growth of the same tumor. but not other tumors. Srivastava and Maki, 1991, *Curr. Topics Microbiol.* 167: 109–123 (1991). The source of the tumor-specific immunogenicity has not been confirmed. Genes encoding heat shock proteins have not been found to exhibit tumor-specific DNA polymorphism. Srivastava and Udono, *Curr. Opin. Immunol.* 6:728–732 (1994). High resolution gel electrophoresis has indicated that gp96 may be heterogeneous at the molecular level. Feldweg and Srivastava,*Int. J. Cancer* 63:310–314 (1995). Evidence suggests that the source of heterogeneity may be populations of small peptides adherent to the heat shock protein, which may number in the hundreds. Id. It has been proposed that a wide diversity of peptides adherent to tumor-synthesized heat shock proteins may render such proteins capable of eliciting an e response in subjects having diverse HLA phenotypes, in contrast to more traditional immunogens which may be somewhat HLA-restricted in their efficacy. Id.

Lukacs et al., *J. Exp. Med.* 178: 343–348 (1993). have reported the transfection of tumor cells with a mycobacterial heat shock protein-encoding gene, and the observation that the transfected cells lose tumorigenicity and induce what appears to be T-cell mediated protection against tumors in mice immunized using the transfected cells. Lukacs et al. suggest that the loss of tumorigenicity could result from the interaction of the heat shock protein with p53 via increased efficiency of chaperone activity to produce proper folding and conformation of otherwise ineffective p53 protein. They further suggest that the highly immunogenic nature of the 65 kD bacterial hsp enhances the recognition of other, tumor-associated antigen molecules.

It has been suggested in the literature that mycobacterial heat shock proteins may play a role in the onset of autoimmune diseases such a rheumatoid arthritis. Thus, the practical utility of such bacterial proteins in vaccines for the treatment of humans is questionable. It is an object of the present invention to provide vaccine compositions which can be used to stimulate an Lmmune response to antigens, including tumor and infectious disease antigens, present in mammalian cells without the introduction of mycobacterial proteins.

SUMMARY OF THE INVENTION

It has now been found that administration of expressible polynucleotides encoding eukaryotic heat shock proteins to mammalian cells leads to the stimulation of an immune response to antigens present in those cells. This makes it possible to stimulate an immune response to treat a subject's disease condition, including an immune response to a tumor or an infectious disease, without having to isolate or characterize an antigen associated with the disease. Thus, the present invention provides a method for stimulating a therapeutic or prophylactic immune response in a mammalian subject by treating the subject or a group of cells from the subject with an expressible polynucleotide encoding a eukaryotic heat shock protein. The expressed heat shock protein may have the same structure as native heat shock proteins, or may be a modified firm adapted to control the trafficking of the expressed heat shock protein within the cells.

BRIEF DESCRIPTION OF THE DRAWINGS

FIGS. 1A–H show tumor formation in mice injected with CMS-5 sarcoma cells and CMS-5 sarcoma cells acutely transfected with BiP-expressing vectors.

DETAILED DESCRIPTION OF THE INVENTION

Figure 1E:
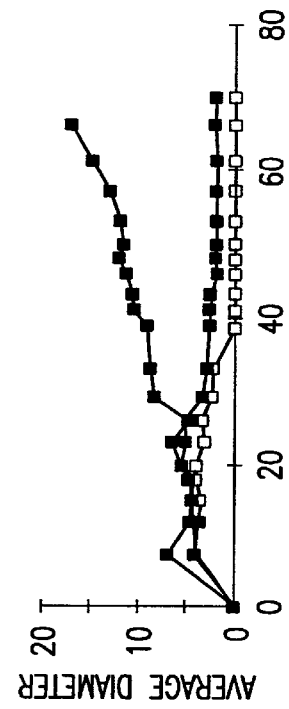

The present invention provides a method for inducing or enhancing an immune response to an antigen present in a target group of cells without requiring prior identification, characterization or isolation of the antigen. The method of the invention may be used to induce an immune response to the antigen in the case where there is no existing detectable disease-related immune response prior to practicing the method, or to enhance the disease-related immune response to a greater level. For purposes of simplicity, the specification and claims of this application will use the term "stimulating an immune response" to encompass both inducing a new immune response and enhancing a pre-existing immune response.

We have found that administration of expressible polynucleotides encoding eukaryotic heat shock proteins to mammalian cells leads to the stimulation of an immune response to antigens present in those cells. While we do not intend to be bound by any particular mechanism, the full potential of our observations is best understood in the context of two mechanistic models which explain the observations.

The first mechanism is based on the fact that heat shock proteins like BiP and gp96 are normally localized in the endoplasmic reticulum and are known to bind peptides and proteins in this location, and the belief that such binding may be a step in the presentation of an antigen to the immune system. Increasing the concentration of one or more heat shock proteins resident in the endoplasmic reticulum may cause an improvement in the efficiency of this process, and thus an increased immune response to the antigens present in the transfected cells.

The second mechanism is based upon the understanding that heat shock proteins and other proteins secreted from the endoplasmic reticulum may be recaptured by receptors known as erd-2 (KDEL) receptors and returned to the endoplasinc reticulum. This recapture process requires the presence of a specific signal on the heat shock protein such as XDEL. XDEL is the single letter amino-acid code for the amino acid sequence variable Asp-Glu-Lcu. Specific carboxy-terminal signal sequences are KDEL (Lys-Asp-Glu-Leu; SEQ ID NO:3) and HDEL (His-Asp-Glu-Leu; SEQ ID NO:4). By eliinating this signal in heat shock proteins which bind to antigens or by otherwise interfering with the ability of the erd-2 receptor to recapture these heat shock proteins, the amount of antigen-associated heat shock protein secreted by a cell and therefore accessible to the immune system can he increased.

In accordance with either of these mechanisms, the stimulation of the immune response which is observed when an expressible polynucleotide encoding a heat shock protein is expressed in the cell flows from an increase in the amount of antigen-associated heat shock protein. Thus, in accordance with one embodiment of the invention there is provided a method for stimulating an immune response to an antigen present in a target group of mammalian cells, comprising administering to the target group of cells a composition effective to increase the amount of antigen-associated heat shock protein present in the cells. This can be accomplished in several ways.

First, the amount of antigen-associated heat shock protein can be increased by administering a polynucleotide encoding a heat shock protein which is expressed to produce recombinant heat shock protein that is processed and transported within the cell in the same manner as wild-type heat shock protein.

Second, the amount of antigen-associated heat shock protein can be increased by administering an expressible polynucleotide encoding a heat shock protein in a modified form adapted to control the trafficking of the expressed heat shock protein within the cells. This would include alterations of heat shock protein which either facilitate its secretion from the cell or its localization and/or retention on the cell. For example, secretion may be facilitated by mutating or eliminating portions of the heat shock protein that serve to retain the heat shock protein in the cell (for example by deleting sequences recognized by the erd-2 receptor such as KDEL or a functionally equivalent sequence or by adding an agent that interferes with binding of heat shock protein to erd-2), or by supplying mutated non-heat shock proteins (e.g. erd-2 mutants) that increase heat shock protein secretion. Alternatively localization and retention may be accomplished by increasing the number and/or strength of retention or retrieval signals (e.g. increasing erd-2 levels) or my by adding to a heat shock protein, a membrane anchor containing additional retention or retrieval sequence as well as transmembrane and cytoplasmic domains (e.g., KKXX at the C-terminal end, or XXRR at the N-terminal end or function equivalents thereof.)

Third, the amount of an antigen-associated heat shock protein can be increased by administering an expressible polynucleotide encoding a peptide or peptide which competitively inhibits the interaction of heat shock proteins with cellular elements to modify the trafficking of those heat shock proteins within the cell.

Preparation of Expressible Polynucleotides

The construction of expressible polynucleotides for use in the three embodiments of the invention share many common elements and use generally well known techniques. These techniques are set forth in-numerous literature references known to persons skilled in the art and so will not be repeated exhaustively here.

Expressible polynucleotide encoding a heat shock protein which is expressed to produce recombinant heat shock protein that is processed and transported within the cell in the same manner as wild-type heat shock protein can be constructed by incorporating a cDNA encoding a wild-type heat shock protein or a modified heat shock protein that retains both its heat shock protein functionality and the XDEL signal sequence into a mammalian expression vector. Genes for various mammalian heat shock proteins have been cloned and sequenced, including, but not limited to, gp96, human: Genebank Accession No. X15187; Maki et al., *Proc. Nat'l Acad. Sci.* 87: 5658–5562 (1990), mouse: Genebank Accession No. M16370; Srivastava et al., *Proc. Nat'l Acad. Sci.* 84:3807–3811 (1987)); BiP, mouse: Genebank Accession No. U16277; Haas et al., *Proc. Nat'l Acad. Sci. U.S.A.* 85: 2250–2254 (1988), human: Genebank Accession No. M19645; Ting et al., DNA 7: 275–286 (1988); hsp70, mouse: Genebank Accession No. M35021; Hunt et al. Gene 87: 199–204 (1990). human: Genebank Accession No. M24743; Hunt et al., Proc. Nat'l Acad. Sci. U.S.A. 82: 6455–6489 (1995); and hsp40 human: Genebank Accession No. D49547; Ohtsuka K., *Biochem Biophys. Res. Commun.* 197: 235–240 (1993).

In general, any type of mammalian expression vector can be used, although those with the highest transfection and expression efficiencies are preferred to maximize the levels of expression. Specific types of vectors which can be employed include herpes simplex viral based vectors: pHSVl (Geller et al. Proc. Natl. Acad. Sci 87:8950–8954 (1990)); recombinant retroviral vectors: MFG (Jaffee et al. Cancer Res. 53:2221–2226 (1993)); Moloney-based retroviral vectors: LN, LNSX, LNCX, LXSN (Miller and Rosman Biotechniques 7:980–989 (1989)); vaccinia viral vector: MVA (Sutter and Moss Proc. Natl. Acad. Sci. 89:10847–10851 (1992)); recombinant adenovirus vectors pJM17 (Ali et al Gene Therapy 1:367–384 (1994)), (Berkner K. L. Biotechniques 6:616–624 1988); second generation adenovirus vector: DE1/DE4 adenoviral vectors (Wang and Finer Nature Medicine 2:714–716 (1996) ); and Adeno-associated viral vectors: AAV/Neo (Muro-Cacho et al. J. Immunotherapy 11:231–237 (1992)). Specific suitable expression systems for this purpose include pCDNA3 (InVitrogen), plasmid AH5 (which contains the SV40 origin and the adenovirus major late promoter), pRC/CMV (InVitrogen), pCMU II (Paabo et al., *EMBO J.* 5: 1921–1927 (1986)), pZip-Neo SV (Cepko et al., *Cell* 37: 1053–1062 (1984)) and pSRα (DNAX, Palo Alto, Calif.).

Expressible polynucleotides encoding any of the various modified forms heat shock proteins described above are constructed using similar techniques. For example, heat shock proteins can be produced which are modified to delete or block the carboxy-terminal XDEL sequence. Such a heat shock protein is adapted to permit the heat shock protein to be secreted from the endoplasmic reticulum and to interfere with the return of the protein to the endoplasmic reticulum that is mediated by the erd-2 receptors because the signal peptide recognized by the erd-2 receptors is missing. Proteins of this type are referred to in the specification and claims of this application as XDEL-negative heat shock proteins.

Expressible XDEL-negative polynucleotides can be constructed by deleting the nucleotides encoding the amino acid sequence XDEL at the carboxy-terminus of the heat shock protein. This can be accomplished by PCR amplification of the wild-type cDNA using a primer that hybridizes in the region immediately adjacent to the portion coding for the XDEL signal, combined with a restriction site to be used for cloning the product into a desired vector for expression of the modified heat shock protein in mammalian cells as described above.

As an alternative to the use of expressible polynucleotides encoding deletion mutants of heat shock proteins, the method of the invention may also employ expressible polynucleotides which encode heat shock proteins in which the carboxy-terminal signal group; KDEL is masked by the addition of additional amino acids to the carboxy-terminal end. The masking amino acids can serve only the masking function, or can be derived from an infectious agent (for example E7/E6 from human papilloma virus) in which case the masking amino acids may also function as an antigen.

Addition of masking amino acids can be accomplished as described in Munro et al., *Cell* 48: 899–907 (1987) in which a mutant (SAGGL; SEQ ID NO:5) having two amino acids added after the XDEL was prepared by cloning in appropriate restriction sites to permit substitution of a sequence including the additional bases, or by PCR amplification of the heat shock proteins using a primer that hybridizes with the bases encoding the XDEL signal and which has additional bases encoding the added nucleotides inserted between the XDEL-encoding bases and the stop codon. The number of additional amino acids does not matter, so long as the added amino acids do not alter the function of the heat shock protein. The nucleotides encoding the masked heat shock protein are then introduced into a mammalian expression vector as described above.

Another method which may be used to increase the amount of antigen-associated heat shock protein in the cells is to modify cytosolic heat shock proteins with an amino-terminal signal which causes the protein to be taken up into the endoplasmic reticulum where it can gain access to the secretory pathway. Amino-terminal signals which can accomplish this function are described in the art, including for example in von Heijne, G., *J. Mol. Biol.* 184: 99–105 (1985). These signals generally comprise a positively-charged amino acid or group of a few amino acids at the amino terminal end of the peptide, a hydrophobic core region and a third region of greater polarity than the hydrophobic region. Such additional signal sequences can be introduced using PCR with a modified primer that includes the bases for the desired amino-terminal amino acids. A representative cytosolic heat shock protein which might be modified in this manner is hsp70.

The expressible polynucleotide used in the method of the present invention may also encode a peptide or protein that competitively inhibits the interaction of heat shock proteins with cellular elements to modify the trafficking of those heat shock proteins within the cell. In particular, the expressible polynucleotide may encode a peptide or protein that includes a carboxy-terminal XDEL signal which will compete with heat shock proteins, including endogenous heat shock proteins, for binding to the erd-2 receptors. This competitive peptide may itself be a heat shock protein, for example BiP, that retains the XDEL signal sequence, or it may be some other peptide or protein with a carboxy-terminal XDEL sequence.

Administration of Expressible Polynucleotides

The resulting expressible polynucleotide is delivered into cells of the subject by ex vivo or in vivo methods, for example as part of a viral vector as described above, or as naked DNA. Suitable methods include infection directly into tissue and tumors, transfection using liposomes (Fraley et al, *Nature* 370: 111–117 (1980)) receptor-mediated endocytosis (Zatloukal, et al., *Ann. N.Y. Acad. Sci.* 660: 136–153 (1992)), particle bombardment mediated gene transfer (Eisenbraun et al., *DNA & Cell. Biol.* 12: 791–797 (1993)) and transfection using peptide presenting bacteriophage. Barry et al. *Nature Medicine* 2: 299–305 (1996).

The expressible polynucleotide may be administered to a subject in need of treatment in order to obtain a therapeutic immune response. The term "therapeutic immune response", as used herein, refers to an increase in humoral and/or cellular in unity, as measured by standard techniques, which is directed toward an antigen associated with the subject's disease condition. Preferably, but not by way of limitation, the induced level of humoral immunity directed toward the antigen is at least four-fold, and preferably at least 16-fold greater than the levels of the humoral immunity directed toward the antigen prior to the administration of the expressible polynucleotide of this invention to the subject. The immune response may also be measured qualitatively. by means of a suitable in vitro assay or in vivo, wherein an arrest in progression or a remission of neoplastic or infectious disease in the subject is considered to indicate the induction of a therapeutic immune response.

A further aspect of the invention is the administration of an expressible polynucleotide in combination with other forms of treatment including surgery, radiation therapy, and chemotherapy, to provide a vaccination against recurrence of cancer. By priming the immune system of subjects to recognize the cancer cells of their own cancers, the immune system will be more prepared to counter a subsequent regrowth, thus improving the prognosis for the subjects. This same type of vaccination can be used to improve a subject's resistance to recurrent diseases, including many parasitic and viral diseases. Thus, the expressible polynucleotides of the invention may be administered to stimulate a prophylactic immune response. The term "prophylactic immune response", as used herein, refers to an increase in long term humoral and/or cellular immunity, as measured by standard techniques, which is directed toward an antigen associated with the subject's disease condition. In general, the prophylactic immune response is measured qualitatively, wherein a delay in the onset of recurring system is achieved.

The subject treated in the method of the invention may be a human or non-human subject.

In various embodiments of the invention, the polynucleotide may encode a heat shock protein derived from the same species or alternatively from a different species relative to the species of the subject.

The cells into which the expressible polynucleotide are introduced may be neoplastic cells or other cancer cells from the subject to be treated or vaccinated. In particular, the method of the invention is usefully applied to treat or vaccinate subjects suffering from cancer including solid tumors and neoplastic disease such as sarcoma, lymphoma, carcinoma, leukemia and melanoma. The method of the invention may also be utilized to stimulate an immune response to infectious diseases, including parasitic, fungal, yeast, bacterial, mycoplasmal and viral diseases, where a particular class of cells can be identified as harboring the infective entity. For example, but not by way of limitation, the cells treated may be infected with a human papilloma virus, a herpes virus such as herpes simplex or herpes zoster, a retrovirus such as human immunodeficiency virus 1 or 2, a hepatitis virus, an influenza virus, a rhinovirus, respiratory syncytial virus, cytomegalovirus, adenovirus, *Mycoplasma pneumoniae*, a bacterium of the genus Salmonella, Staphylococcus, Streptococcus, Enterococcus, Clostridium, Escherichia, Klebsiella, Vibrio, Mycobacterium, amoeba, a malarial parasite, *Trypanosoma cruzi*, etc. Thus, for example, in the case of human papilloma virus (HPV), the expressible polynucleotide could be introduced into epithelial cells infected with HPV from the subject to be treated.

The method of the invention can be practiced using various compositions. One such composition of matter is a recombinant vector comprising a promoter system effective to promote expression of the vector in mammalian cells; and a region encoding a XDEL-negative heat shock protein. The vector may be one in which the bases encoding a XDEL-signal have been deleted from the region encoding the heat shock protein, or one in which additional bases have been added to the region encoding the heat shock protein to mask the XDEL-signal in the expressed product. An exemplary vector would include gp96, preferably human gp96, as the heat shock protein.

A further composition of matter in accordance with the invention is a recombinant vector comprising a promoter system effective to promote expression of the vector in mammalian cells; and a region encoding a cytosolic heat shock protein such as hsp70 to which a signal comprising a positively-charged amino acid or group of a few amino acids at the amino terminal end of the peptide, a hydrophobic core region and a third region of greater polarity than the hydrophobic region is attached to promote uptake of the expressed cytosolic heat shock protein by the endoplasmic reticulum has been added.

The invention will now be further described by way of the following non-limiting examples.

EXAMPLE 1

Preparation of XDEL Deletion Mutants

The preparation of mammalian expression vectors encoding full-length and KDEL-deleted Drosophila BiP cDNAs (dBiP, also referred to a grp78) is described in Munro et al., *Cell* 48: 899–907 (1987). The expression vector encoding dBIP with a KDEL deletion (KDEL-deleted dBiP, SAGM2) has the KDEL signal replaced with a c-myc sequence in a modified AHP2 plasmid. A further construct, WT dBiP (SAGMK1) has the c-myc sequence inserted between the KDEL signal and the balance of the dBiP.

Wild type mouse BiP cDNA was cloned into plasmid pBSBiP. Haas, *Proc. Nat'l Acad. Sci. USA* 85: 2250–2254 (1988). In this plasmid, the BiP sequence is flanked by BamH I sites. The BamH I fragment was therefore recovered from pBSBiP and cloned into the BamH I site of mammalian expression vector pCDNA3 (In-Vitrogen). Mouse EDEL-deleted BiP was constructed using pCDNA3 by cloning the Bgl II-EcoR V PCR fragment (nucleotide 1360 to nucleotide 1981) of BiP using two oligonucleotide primers complementary to BiP. The nucleotides coding for the last four amino acids (KDEL) were omitted, and a stop codon and an EcoR V restriction site put in its place.

EXAMPLE 2

Preparation of Tumor Cells Expressing BiP

CMS-5 sarcoma cells, a methylocholanthrene-induced fibrosarcoma of BALB/c mouse origin, were adapted to culture and grown in DMEM medium (Gibco Life Technologies, Inc.) supplemented with 10% FCS. Sub-confluent monolayers ($2 \times 10^9$ cells) were transfected with 2 ug of mammalian expression vector containing BiP or KDEL-deleted BiP using lipofectamine (Gibco) according to the manufacturer's directions. Briefly, the expression vector and 6 ul of lipofectamine were diluted separately in 100 uL serum-free medium (OPTI-MEM® I Reduced Serum Medium, Gibco-BRL). The two solutions were then mixed and incubated at room temperature for 45 minutes to allow formation of DNA-liposome complexes. 800 uL OPTI-MEM® was added to the complexes, mixed, and overlaid onto rinsed cells. After a 6 hour incubation at 37° C., 1 mL growth medium containing 20% FCS was added. Fresh medium was added to the cells 24 hours post-transfection.

Stable clones were selected by adding 800 ug/mL geneticin (Gibco-BRL) to the cells 72 hours later. The selection medium was changed every 3 days. Colonies of stably transfected cells were seen after 10 to 14 days. Expression of BiP for each clone picked was assayed for by radiolabeling. Newly synthesized BiP was detectable by immunoprecipitation and gel electrophoresis.

Acutely (transiently) BiP expressing clones were trypsinized and used for animal injection 60 hours post-transfection.

EXAMPLE 3

Vaccination With BiP Expressing Tumor Cells

Figure 1F:
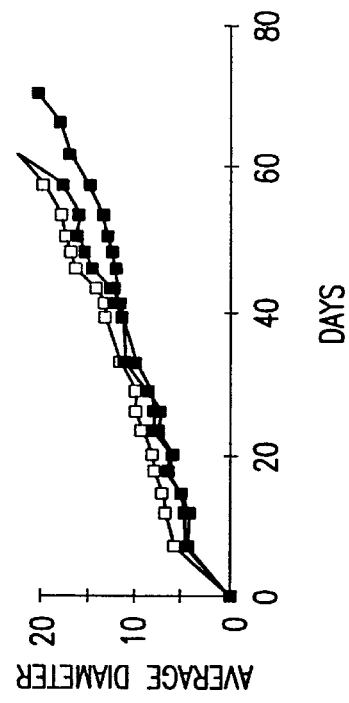
Figure 1G:
Figure 1H:
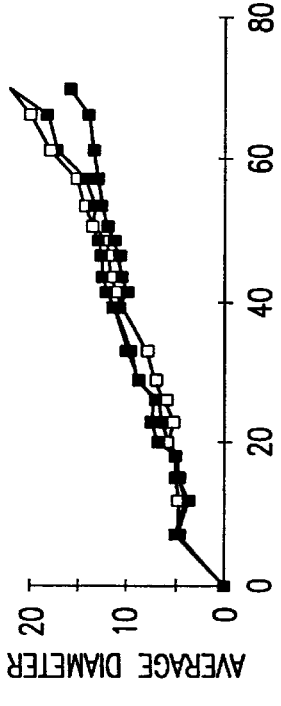

Freshly prepared acutely transfected CMS-5 sarcoma cells prepared in accordance with Example 2 were prepared for use in vaccination of mice by trypsinization and then washing three times in PBS. $2 \times 10^6$ cells were injected intradermally into the abdomen of CB6F-1/J [Balb/c×C57BL/6 F1] mice (Jackson Laboratories) and monitored for tumor growth over a 90 day period. The results are summarized in Table 1 and shown graphically in FIGS. 1A–H. As shown, injection with the parental CMS-5 sarcoma cells, with mock transfected cells, and with cells transfected with KDEL-deleted vectors led in all cases to the formation of tumors. Tumors also developed in one control mouse where the cells were transfected with the vector only (no BiP). On the other hand, only one of six mice transfected with the complete wild-type drosophila BiP (including the c-myc) or wild-type mouse BiP developed tumors.

TABLE 1

| Cell Line | Number of Tumor Free Mice per number of mice injected | Percent Tumor Free Survivals |
| --- | --- | --- |
| Parental CMS5 | 0/4 | 0% |
| Mock Transfected | 0/3 | 0% |
| Vector Only | 1/3 | 33% |
| Mouse BiP wild type | 2/3 | 66% |
| Mouse BiP KDEL deleted | 0/3 | 0% |
| Drosophila BiP wild type | 3/3 | 100% |
| Drosophila BiP KDEL deleted | 0/3 | 0% |

EXAMPLE 4

Figure 2A:
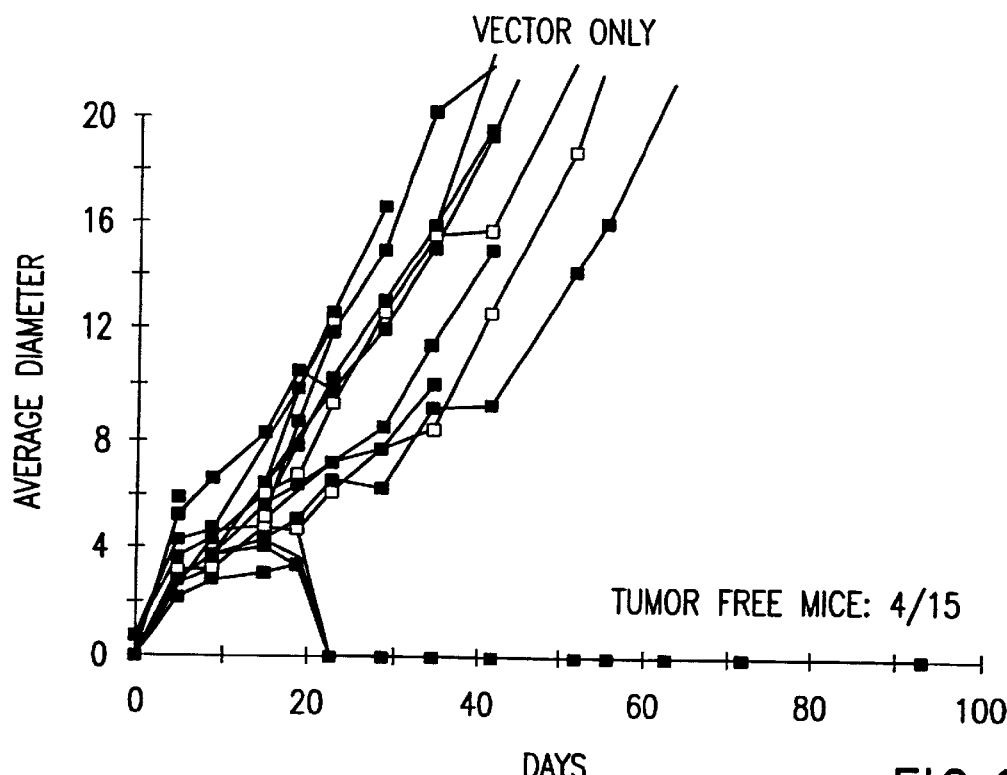
FIGS. 2A–F show tumor formation in mice injected with CMS-5 sarcoma cells and CMS-5 sarcoma cells stably transfected with BiP-expressing vectors.
Figure 2B:
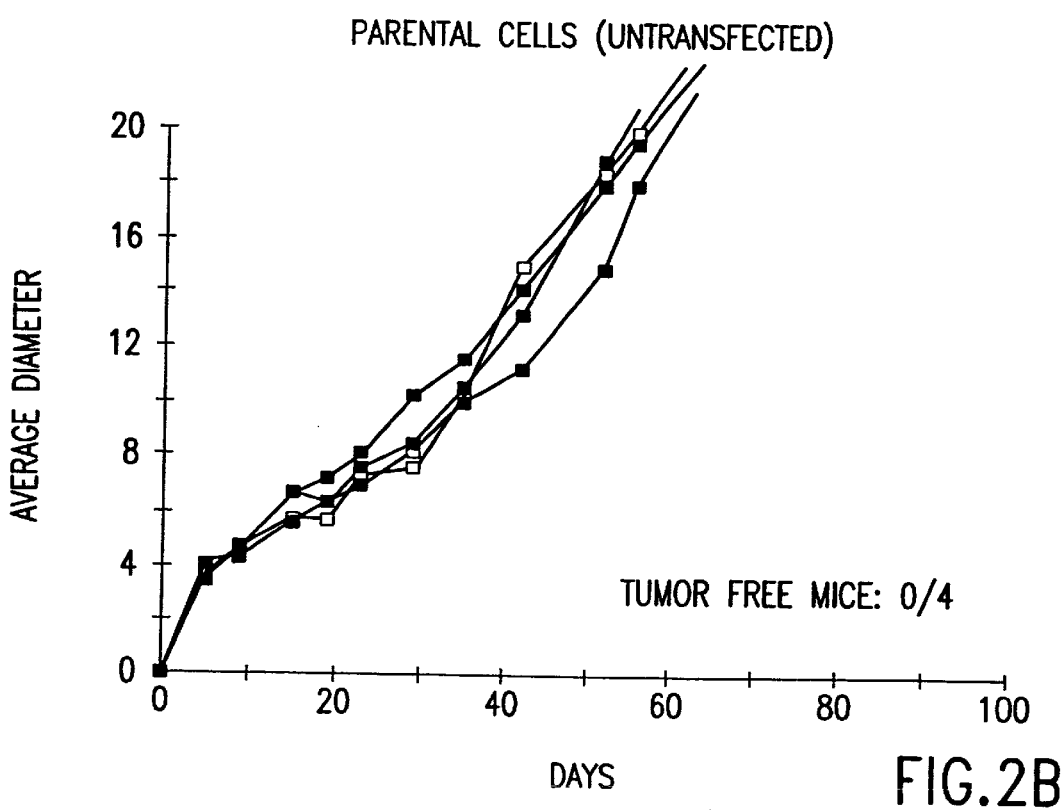
Figure 2C:
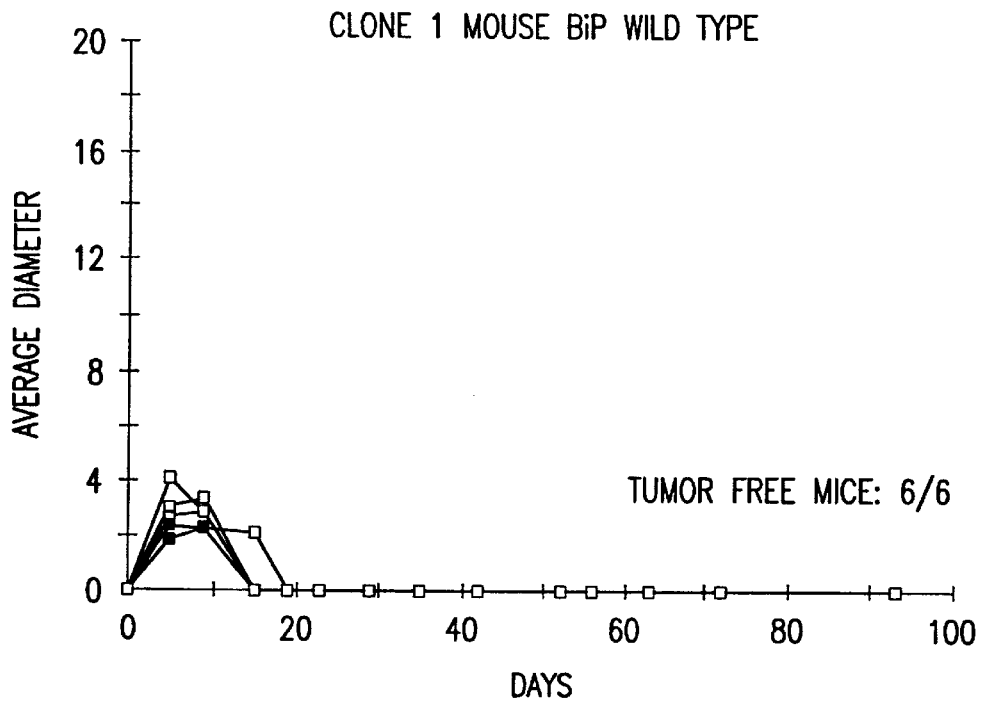
Figure 2D:
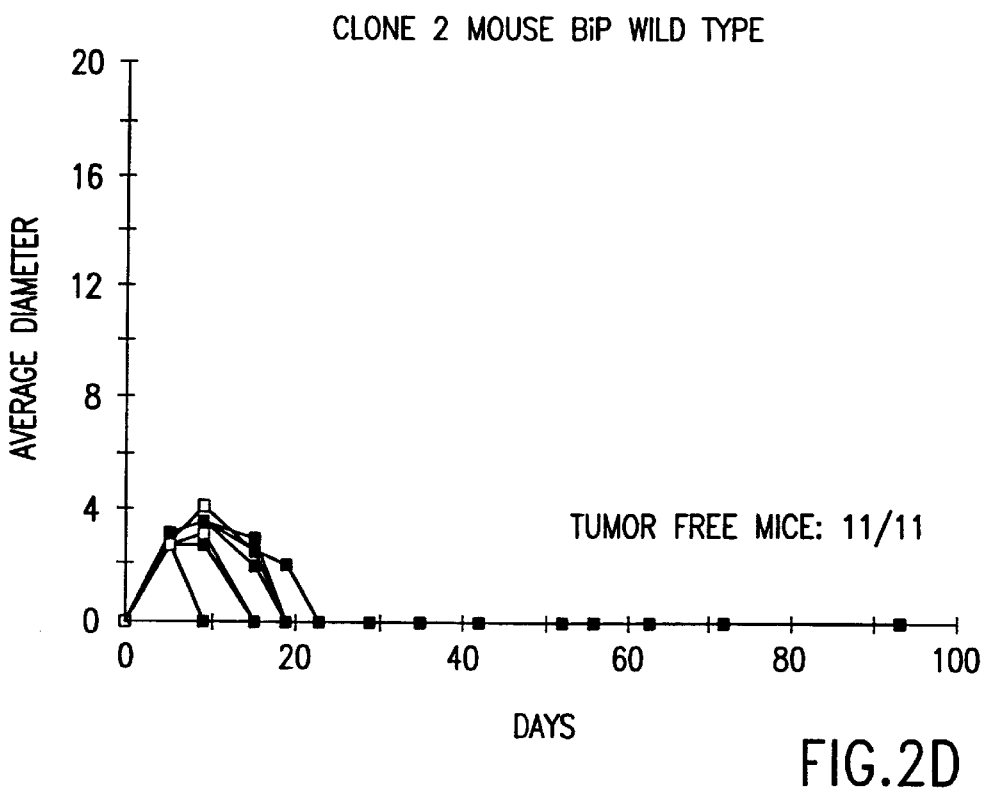
Figure 2E:
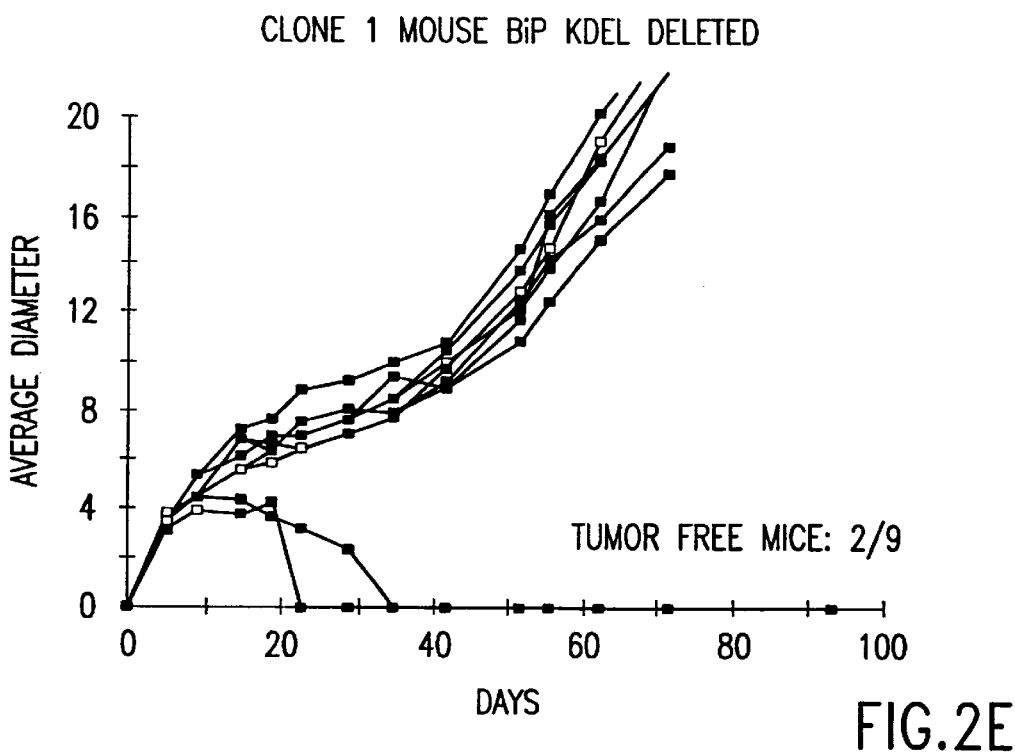
Figure 2F:
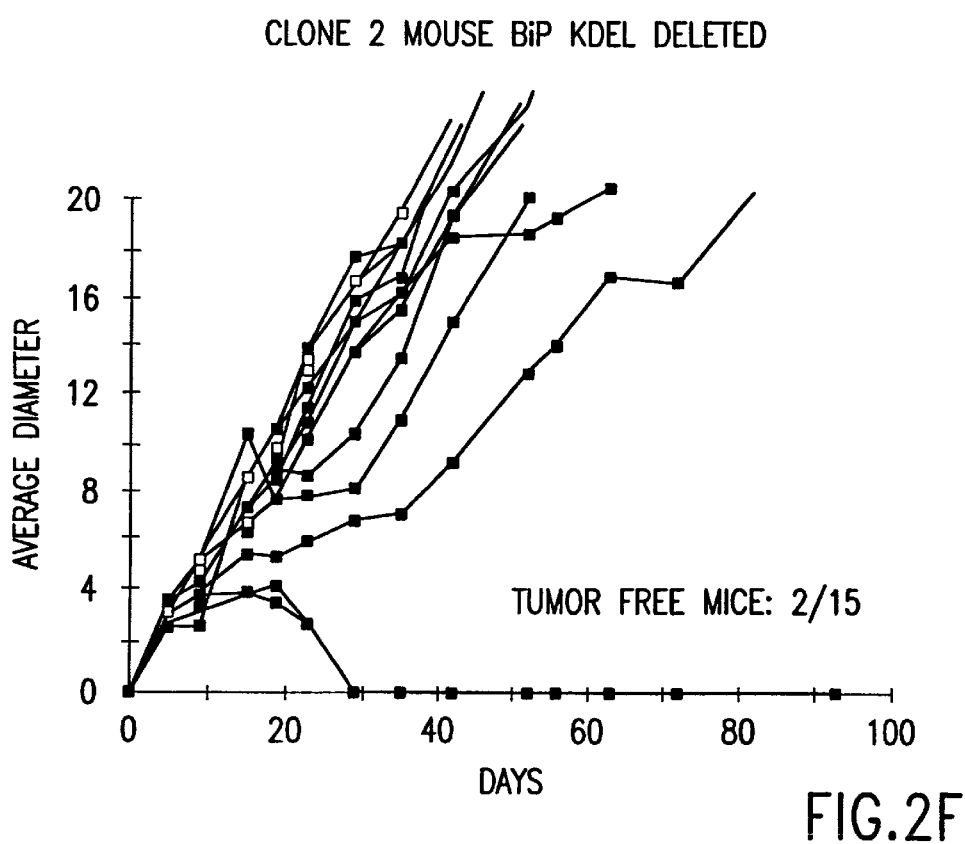

The experiment of Example 3 was repeated using larger groups of mice and using two different clones of stable mouse BiP-expressing transfected cells. As shown in Table 2 and FIGS. 2A–F, the results were essentially the same, with none of the mice injected with the vector expressing wild-type mouse BiP having any detected tumor formation.

TABLE 2

| Cell Lines | Number of Tumor Free mice per number mice injected | Percent Tumor Free Survivals |
| --- | --- | --- |
| Parental CMS5 | 0/4 | 0% |
| Vector Only | 4/15 | 27% |
| Mouse BiP wild type: clone 1 | 6/6 | 100% |
| Mouse BiP wild type: clone 2 | 11/11 | 100% |
| Mouse BiP KDEL deleted: clone 1 | 1/9 | 11% |
| Mouse BiP KDEL deleted: clone 2 | 2/15 | 13% |

EXAMPLE 5

Tumor-free mice that had been injected with the wild-type BiP expression vector in the experiment of Example 4 were rechallenged after an interval of two months by injection of $2\times10^6$ or $10\times10^6$ CMS-5 sarcoma cells into the left flank of each mouse. Unimmunized CB6F-1/J mice of the same age group that had not been previously immunized were injected at the same time with $2\times10^6$ CMS-5 sarcoma cells as controls. As shown in Table 3, none of the previously immunized mice developed detectable tumors, while all three of the control mice developed tumors and died.

TABLE 3

| Rejected Tumor | Number of Tumor Free Mice/Number of Mice Injected | % Survivals |
| --- | --- | --- |
| Mouse BiP wild type: clone 1 | 3/3 | 100% |
| | 3/3 | 100% |
| Mouse BiP wild type: clone 2 | 5/5 | 100% |
| | 6/6 | 100% |
| Control | 0/3 | 0% |

EXAMPLE 6

Construction of Vector Expressing gp96

To create an expressible vector encoding GP96, the coding region of murine GP96 (mGP96) was digested with BamH I, blunted with Klenow and cloned into the mammalian expression vector pRC/CMV (InVitrogen) which has been digested with Xba I and also blunted with Klenow. The resulting plasmid, p96/CMV was then used as template for generating a fragment spanning nucleotides 1653 to 2482 that lacks the nucleotides encoding the amino acids KDEL. The primers used for amplification of this fragment were 5' primer:

GCGGATCCTAGTTTAGACCAGTATGTC [SEQ ID No. 1]

3' primer:

CCGAATTCGGGCCCCAAT TTACTCTGTAGATTCCTTTTCGTTT [SEQ ID No. 2]

The restrictions sites for BamH I in the 5'-primer and EcoR I and Sal I in the 3'-primer are shown in bold italics. A stop codon (shown underlined) is provided four nucleotides from the Sal I restriction site in the 3'-primer. The BamH I/EcoR I PCR fragment was subcloned into pBlueScript II (Stratagene) to further amplify the amount of DNA. The amplified DNA was then digested with PflM I and Apa I, gel purified and subcloned into p96/CMV to give pMS215 which codes for KDEL-deleted gp96.

EXAMPLE 7

Vaccination With GP96 Expressing Vectors

Plasmids encoding the wt mGp96 (pMS216) and KDEL deleted mGp96 (215) are transfected into CMS-5 sarcoma cells as described in Example 2. 86 h post transfection, the acutely transfected CMS-5 sarcoma cells are trypsinized, washed in PBS and prepared for use in vaccination of mice as described in Example 3.

Various publications are cited herein, the contents of which are hereby incorporated by reference in their entireties.

What is claimed is:

1. A recombinant vector comprising an expressible polynucleotide encoding a eukaryotic cytosolic heat shock protein having an amino terminal signal sequence and a carboxy-terminal retention sequence comprising an XDEL sequence recombinantly fused to the carboxy-terminus of the heat shock protein, wherein a promoter system is operatively linked to said expressible polynucleotide.

2. The recombinant vector of claim 1 wherein the XDEL sequence is KDEL.

3. The recombinant vector of claim 1 wherein the heat shock protein is a cytosolic hsp 70.

* * * * *

SEQUENCE LISTING

<160> NUMBER OF SEQ ID NOS: 5

<210> SEQ ID NO 1
<211> LENGTH: 27
<212> TYPE: DNA
<213> ORGANISM: mouse

-continued

```
<400> SEQUENCE: 1
gcggatccta gtttagacca gtatgtc                                           27

<210> SEQ ID NO 2
<211> LENGTH: 44
<212> TYPE: DNA
<213> ORGANISM: mouse

<400> SEQUENCE: 2
ccgaattcgg gccccaattt actctgtaga ttccttttct gttt                        44

<210> SEQ ID NO 3
<211> LENGTH: 4
<212> TYPE: PRT
<213> ORGANISM: eukaryotic

<400> SEQUENCE: 3

Lys Asp Glu Leu
 1

<210> SEQ ID NO 4
<211> LENGTH: 4
<212> TYPE: PRT
<213> ORGANISM: eukaryotic

<400> SEQUENCE: 4

His Asp Glu Leu
 1

<210> SEQ ID NO 5
<211> LENGTH: 5
<212> TYPE: PRT
<213> ORGANISM: eukaryotic

<400> SEQUENCE: 5

Ser Ala Gly Gly Leu
 1               5
```